United States Patent [19]

Yabe

[11] Patent Number: 5,309,895
[45] Date of Patent: May 10, 1994

[54] ENDOSCOPE APPARATUS PRODUCING VIDEO SIGNALS FROM IMAGING SIGNALS AT ILLUMINATING AND NON-ILLUMINATING PERIODS

[75] Inventor: Hisao Yabe, Hachioji, Japan
[73] Assignee: Olympus Optical Co., Ltd., Tokyo, Japan
[21] Appl. No.: 904,595
[22] Filed: Jun. 26, 1992
[30] Foreign Application Priority Data Oct. 4, 1991 [JP] Japan .................................. 3-257871

[51] Int. Cl.[5] .......................... A61B 1/06; H04N 7/18
[52] U.S. Cl. .......................................... 128/6; 348/67
[58] Field of Search ....................... 128/6, 4, 7–10; 358/98, 42, 43, 213.16, 213.19, 228; 354/62

[56] References Cited

U.S. PATENT DOCUMENTS 4,604,992  8/1986  Sato .
4,754,328  6/1988  Barath et al. .
4,963,960 10/1990  Takami .................................. 358/98
5,007,407  4/1991  Kikuchi .................................. 128/6

Primary Examiner—Richard J. Apley
Assistant Examiner—John P. Leubecker
Attorney, Agent, or Firm—Armstrong, Westerman, Hattori, McLeland & Naughton

[57] ABSTRACT

A CCD for imaging a subject is driven by a CCD driving circuit. An observation image of the subject obtained by the CCD being driven becomes an output signal of the CCD and is converted into a digital signal by an A/D converter through a preprocessing circuit including an amplifying circuit, low-pass filter and sample hold circuit. While the signal of the observation image converted by the A/D converter when the subject is illuminated is stored in a first memory, the signal of the observation image when the subject is not illuminated is stored in the second memory. The signals stored in the first memory and the second memory are instantaneously read and supplied to a subtracting circuit. In the subtracting circuit, operation process for extracting a signal in which an imaging signal during non-illumination is subtracted from an imaging signal during illumination is carried out. The extracted signal is converted into an analog signal by a D/A converter to supply the signal to a video processing circuit, and then, a standard video signal is produced.

17 Claims, 6 Drawing Sheets

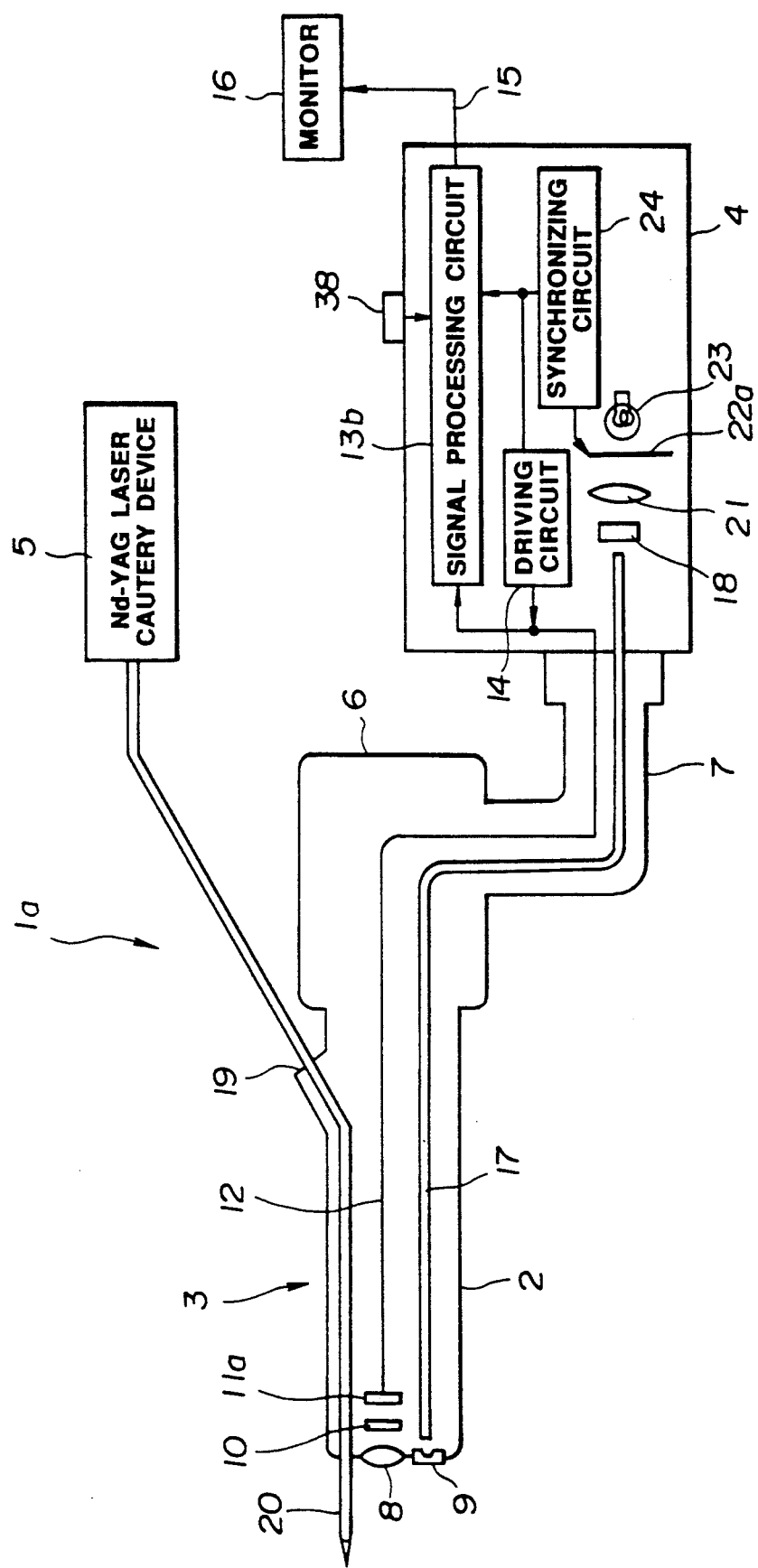

ENDOSCOPE APPARATUS PRODUCING VIDEO SIGNALS FROM IMAGING SIGNALS AT ILLUMINATING AND NON-ILLUMINATING PERIODS

BACKGROUND OF THE INVENTION

1. Field of the Invention

The present invention relates to an endoscope apparatus which periodically irradiates a subject with illuminating light to produce a video signal from imaging signals at an illuminating period and a non-illuminating period.

2. Description of the Related Art

Recently, there has come into use an electronic endoscope apparatus provided with a solid state imaging device, such as a CCD or MOS at the tip part of the endoscope, or endoscope apparatus fitted with a TV camera at the eyepiece part of the endoscope. The aforesaid endoscope apparatus observes the body cavity by inserting an elongated insertable part into the body cavity or, for example, enabling laser treatments to stop bleeding or to cauterize malignant tissue, such as cancer by inserting a laser device into treatment tool channels.

Cautery treatments using the laser device previously have set laser output and a laser applying time based on the result of animal experiments or theoretical experiments to pursue clinical examination. In the case of a treatment in the body cavity, when a solid state imaging device was exposed to light, the luminance of an observation image of the treatment part rose so as to produce a partially white picture, called "whiteout," because the intensity of a laser beam was too strong. Thus, a real-time cauterizing state could not be observed. Therefore, there was a danger of bleeding or perforating by deep cauterization, or there was also danger of cauterizing the part other than the treatment part. To the contrary, the part to be cauterized was insufficiently cauterized, so that the treatment was incomplete.

Then, in order to prevent the whiteout of an observation image in the aforesaid treatment part, for example, when an ND-YAG laser is used, it has been proposed to provide a laser beam cut filter for eliminating infrared rays in an objective optical system and to remove the effect of a YAG laser beam on the observation image.

However, the intensity of the laser beam was strong, and infrared rays in extensive wavelength ranges were generated when the cautery part was burned during the period in which the laser beam was applied. Therefore, it was impossible to eliminate all of these infrared rays by the laser beam cut filter. Also, when the cautery part begins to burn, not only the image became "whited-out" but also the cauterization did not have a favorable effect on the treatment.

Further, the aforesaid YAG laser beam is invisible because it is an infrared laser beam, so that a visible light (such as a He—Ne laser) laser probe for identifying the treatment part is generally provided for guiding light on the same axis as in a YAG laser probe. Since the intensity of the guiding light is constant, the ratio of illuminating light to guiding light changes with endoscopes to be used. Thus, which part is guided cannot be seen clearly when the intensity of the guiding light is much weaker than the illuminating light, and whiteout occurs when the intensity of the guiding light is much stronger than the illuminating light.

In order to solve the aforesaid problem, for example, the invention in which a filter for attenuating guiding light can be selectively used is indicated in the Gazette of Japanese Patent Laid-Open No. 266049/1987. However, in this reference, whiteout of a solid state imaging device cannot be completely prevented because, for example, a cautery part starts burning. Also, an endoscope apparatus in which a laser beam is not sent out during an imaging period of imaging means by radiation of illuminating light by synchronizing the radiation of the illuminating light and the radiation of a laser beam is proposed in the Gazette of Japanese Patent Laid-Open No. 94644/1986. However, a smearing of a solid state imaging device is generated, so that the device has a problem of reducing the quality of the images.

As mentioned above, in the endoscope apparatuses currently in use, when a laser beam and guiding light were sent out when a part is treated using a laser device, a solid state imaging device was exposed to light, so that whiteout might occur at the treatment. Also, when observation by X-ray irradiation and treatment by ultrasonic waves were used at the same time, the X-rays and ultrasonic waves had been superimposed on an observation image of a CCD or the like as noise. In addition, when the endoscope apparatus was used in a place easily affected by outdoor daylight, the contrast of the image had declined and colors of the image had deteriorated. Thus, there were cases in which a real-time subject image from the endoscope could not be observed clearly.

SUMMARY OF THE INVENTION

The object of the present invention is to provide an endoscope apparatus which can obtain a subject image illuminated by illuminating light by satisfactorily preventing the deterioration of an image affected by light other than the illuminating light for observation, such as invisible light including an infrared laser used for an endoscope apparatus, visible light including guiding light for guiding laser treatment tools, X-rays and ultrasonic waves used with an endoscope, and burning light and outdoor daylight.

Another object of the invention is to provide an endoscope apparatus which can remove optically harmful effects including light fog or flare on an image by illuminating light by the effect of light other than illuminating light.

Another object of the invention is to provide an endoscope apparatus which can delete fixed pattern noise including a flaw of a white spot which is especially a problem in a low luminance band or a flaw of a black spot which is a problem in a high luminance band and the other fixed pattern noises which are problems in all bands.

An endoscope apparatus of the present invention comprises:

an insertable part for inserting into an object, illuminating means transmitting illuminating light through the insertable part, for periodically illuminating an object according to a cycle having a same period an illuminating period and a non-illuminating period, imaging means for imaging the object during the illuminating period and the non-illuminating period, means for at least partially removing the effect of illumination other than said illuminating light including signal operating means for producing a difference signal between an imaging signal from the imaging means in a first period, including at least a part of the illuminating period in a cycle of the illuminating period and the non-illuminating period and an imaging signal from the imaging means in a second period, removing the first period from a cycle of the illuminating period and the non-illuminating period, and video signal producing means for producing a video signal from the difference signal from the signal operating means.

The signal operating means operates the difference signal between the signal of the imaging means in the first period and the signal of the imaging means in the second period. The video signal producing means produces the video signal from the difference signal.

BRIEF DESCRIPTION OF THE DRAWINGS

FIG. 1 is a block diagram showing the structure of a signal processing circuit;

FIGS. 2(a), 2(b), 2(c), 2(d) and 2(e) are timing charts explaining a completely removing mode and a 3/4 removing mode;

FIG. 3 is a block diagram of an endoscope apparatus;

FIGS. 5 to 8 relate to the third embodiment;

FIG. 5 is a block diagram of an endoscope apparatus;

FIG. 6 is an illustration showing the structure of a rotary filter;

FIG. 7 is a block diagram showing the structure of a signal processing circuit; and FIGS. 8(a), 8(b), 8(c), 8(d) and 8(e) are timing charts explaining the operation of the endoscope apparatus.

DETAILED DESCRIPTION OF THE PREFERRED EMBODIMENTS

The embodiments of this invention will be explained below in reference to the drawings.

Figure 3:
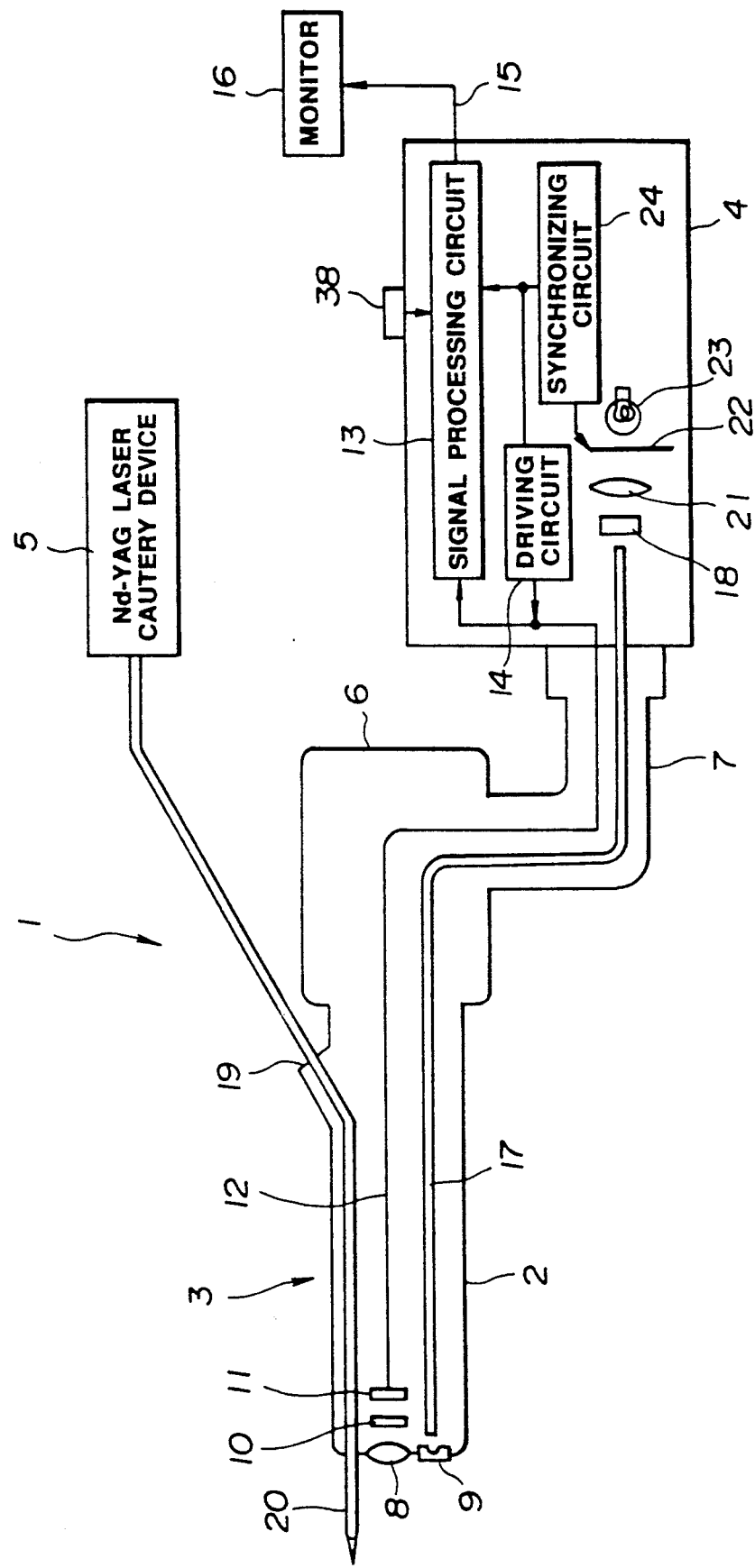

As shown in FIG. 3, for example, an endoscope apparatus 1 of the first embodiment used to cauterize a treatment part consists of an endoscope 3 having an elongated insertable part 2 inserted into the body cavity, an endoscope control device 4 for controlling a light source and a solid state imaging device of the endoscope 3 mentioned below, and an Nd-YAG laser cautery device 5 for controlling a laser probe inserted into a treatment channel (not illustrated) of the endoscope 3.

An operating part 6 is provided on the side at hand of the insertable part 2 of the endoscope 3. A universal cord 7 is extended from the side of the operating part 6 and connected to the endoscope control device 4. An objective lens 8 and an illumination lens 9 are arranged on the side of the tip surface of the insertable part 2. At the rear of the objective lens 8, a solid state imaging device including a CCD 11 observing through a band cut filter 10 is arranged. The CCD 11 is connected to a signal processing circuit 13 and a CCD driving circuit 14 provided in the endoscope control device 4 through a signal line 12. The signal processing circuit 13 transmits an observation image to a monitor 16 through a connecting cable 15.

A tip of a light guide fiber bundle 17 approaches the rear end of the illuminating lens 9. The light guide fiber bundle 17 is inserted into the endoscope 3 so as to optically connect the opposite end of the light guide fiber bundle 17 to a diaphragm device 18 provided in the endoscope control device 4. In addition, as an example of a treatment tool, for example, a laser probe 20 consisting of light fibers is inserted from an insertion inlet 19 which opens at the side of the operating part in a channel for inserting treatment tools (not illustrated) provided in the endoscope 3 and detachably connected to the Nd-YAG cautery device 5 through a connector (not illustrated) provided at the proximal end of the laser probe 20.

The band cut filter 10 has a transmission factor of 1/10000 –1/100000 for the wavelength of 1060 nm and prevents the CCD from breaking by a strong laser beam. Then, an interline type CCD, which is an instantaneous read type CCD, having sensitivity mainly in a visible light range or a frame transfer type CCD is used as the CCD 11. In the first embodiment, frame accumulation of 60 frames/second and a CCD 11 of a frame read type are used. Further, the CCD 11 is a color CCD having a color mosaic filter.

In the endoscope control apparatus 4, a signal processing circuit 13 connected to the CCD 11 through the signal line 12, a CCD driving circuit 14 and the diaphragm device 18 to which the light guide fiber bundle 17 is optically connected are arranged and also, a converging lens 21, a rotary filter 22 and an illuminating light source 23 are arranged at the rear of the diaphragm device 18. The illuminating light source 23 is a white color illuminating lamp of a regular lighting type. The rotary filter 22 makes illuminating light from the illuminating light source 23 illuminate and non-illuminate periodically in response to the signal from a synchronizing circuit 24 provided in the endoscope control apparatus 4 to illuminate a subject in the body cavity. That is, the rotary filter 22 transmits and cuts off the illuminating light from the illuminating light source at intervals of 1/60 second by corresponding to the CCD 11 (duty ratio 50%). Also, the synchronizing circuit 24 supplies a synchronizing signal to the signal processing circuit 13 and the CCD driving circuit 14.

Figure 1:
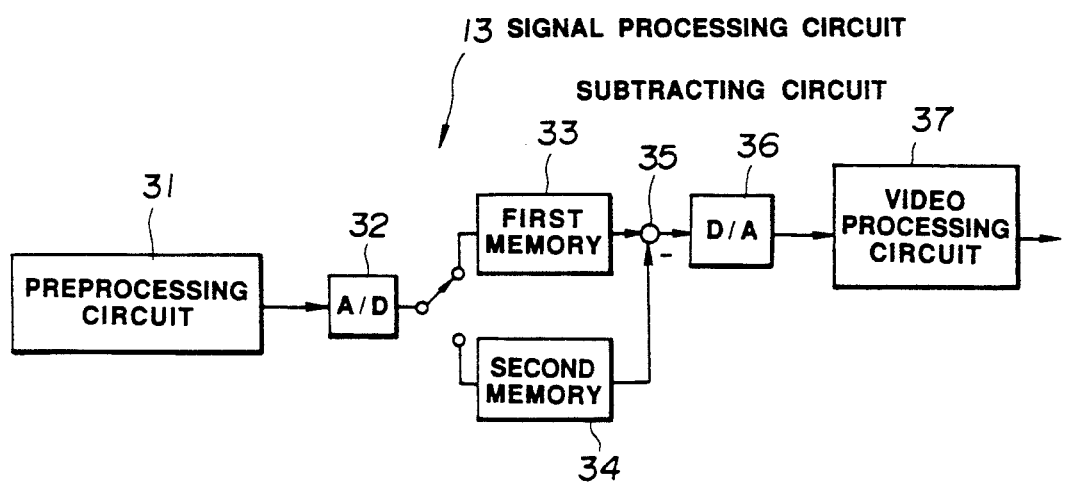
FIGS. 1 to 3 relate to the first embodiment.

In regard to FIG. 1, the structure of the signal processing circuit 13 provided in the endoscope control apparatus 4 will be explained.

The CCD 1 is driven by the CCD driving circuit 14 after receiving a synchronizing signal from the synchronizing circuit 24. The observation image of the subject obtained by the drive of the CCD 11 is converted into a digital signal at an A/D converter 32 through a pre-processing circuit 31 including an amplifying circuit (not illustrated), low-pass filter and sample hold circuit. Of the signals converted by the A/D converter 32, while the signal of the observation image when the subject is illuminated is stored in a first memory 33, the signal of the observation image when the subject is not illuminated is stored in a second memory 34. The signals stored in the first memory 33 and the second memory 34 are instantaneously read and supplied to a subtracting circuit 35. An operation process for extracting a signal in which an imaging signal during non-illumination of the subject is subtracted from an imaging signal during illumination of the subject is performed, so that the extracted signal is converted into an analog signal by a D/A converter 36 and supplied to a video processing circuit 37. Then, a standard video signal is produced. Accordingly, a subject image is displayed on a picture plane of the monitor 16 by the standard video signal. At this moment, the image displayed on the monitor 16 is processed so as to display the same image on A and B fields in the video processing circuit 37.

Also, in the first embodiment, a completely removing mode which can completely remove an effect of light including a laser beam and burning light other than illuminating light, and a ¾ removing mode for removing only ¾ of the effect of the light including a laser beam and burning light other than illuminating light are provided. The completely removing mode can be switched to the ¾ removing mode by a changing-over switch 38.

The operation of the endoscope apparatus 1 formed as stated above will be explained.

Two kinds of modes are provided in the endoscope apparatus 1 to obtain an observation image on the picture plane of the monitor 16. Each mode will be explained on reference to FIG. 2.

Figure 2:
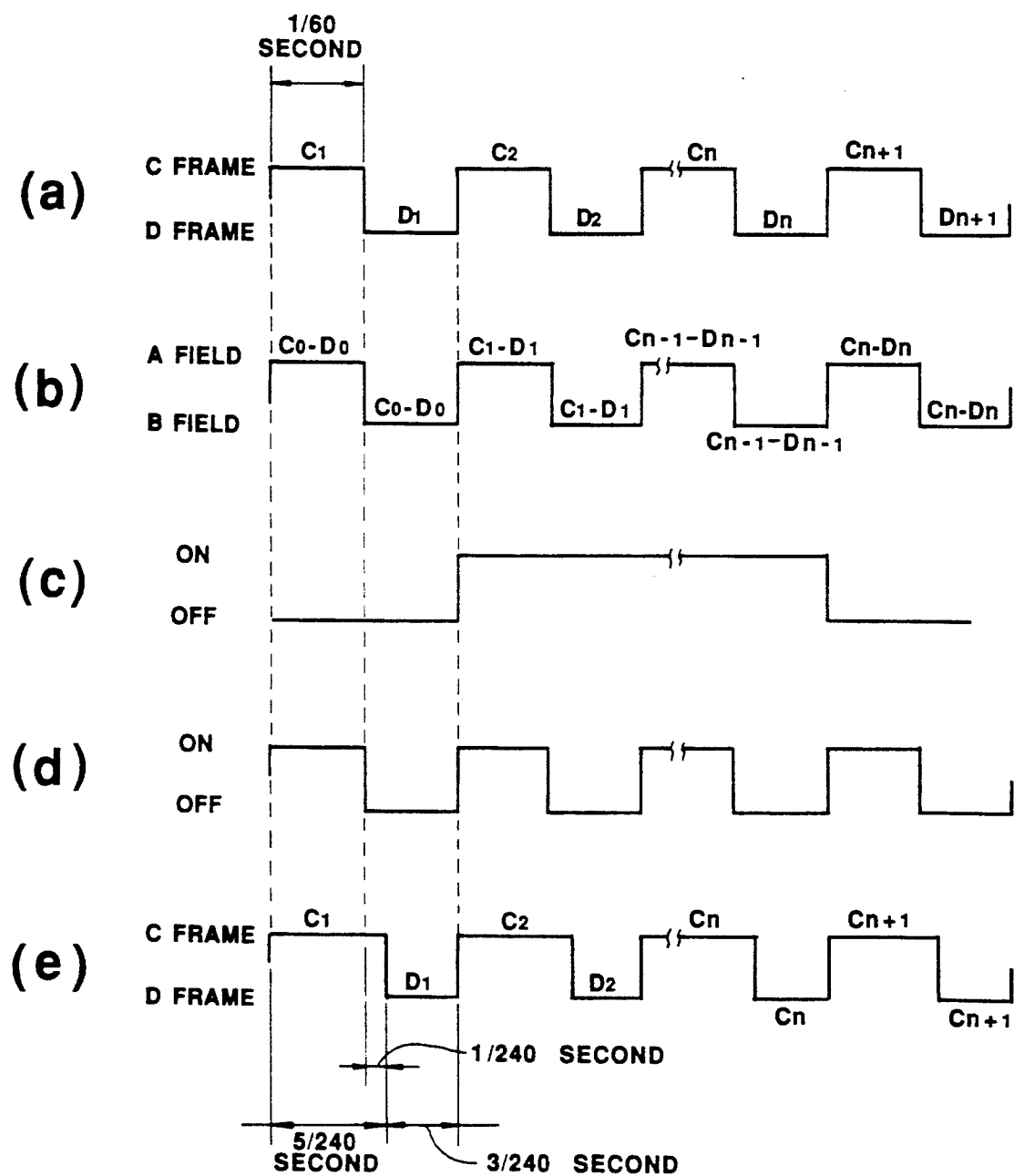

(a) in FIG. 2 is a timing chart showing an imaging frame of the completely removing mode. (b) is a timing chart showing the contents indicated. (c) is a timing chart showing laser radiation. (d) is a timing chart showing turning on and off the illuminating light. (e) is a timing chart showing an imaging frame of the ¾ removing mode.

First of all, the completely removing mode will be explained.

As shown in FIG. 2(a), in the completely removing mode, the imaging time of both C and D frames of the imaging frame is 1/60 second. As shown in FIG. 2(d), the illuminating light also repeats illumination and non-illumination at intervals of 1/60 second. As shown in FIG. 2(a), the observation image is imaged on the C frame of the imaging frame when illuminated and it is imaged on the D frame of the imaging frame when non-illuminated. That is, an observation image C1 when it is illuminated by illuminating light is imaged on the C frame and an observation image D1 when it is not illuminated is imaged on the D frame. Then, as shown in FIG. 2(b), an observation image C0-D0 of 1/30 second earlier appears on the A and B fields in the monitor. Then, at the next cycle, an observation image C2 when it is illuminated is imaged in the C frame and an observation image D2 when it is not illuminated is imaged in the D frame. Then, an observation image C1-D1 of 1/30 second earlier repeatedly appears on the A and B fields.

Thus, when the subject is periodically illuminated, a laser for cauterizing is radiated. At this moment, respective laser illuminating time for the C frame and D frame of the imaging frame becomes about half of the whole laser radiating time. Also, because the laser radiation is switched by a foot switch (not illustrated), the switching of the imaging frames at rising and falling of the laser radiation does not completely coincide. Therefore, the effect of only two fields of the laser beam is generated on the picture plane in the monitor at the beginning and at the end of the laser radiation, respectively. However, the display is affected only for 1/30 second by the laser beam, so that it is not a problem practically.

As stated above, in the completely removing mode, the imaging time of the C frame is equal to the imaging time of the D frame in the imaging frame, so that the laser beam radiating time when the subject is illuminated and the time when the subject is not illuminated are the same. Accordingly, while an operation process is conducted to extract a signal in which an imaging signal during a period of non-illumination is subtracted from an imaging signal during illumination by the subtracting circuit 35, the extracted signal is video-processed at the video processing circuit 37 so as to display the signal on the A and B fields in the monitor 16 As a result, a subject image is applied only by illuminating light without having an effect by a laser beam or the like is displayed on the monitor 16. Also, at the same time, an effect of burning light is removed.

This mode is suitable for a contact type laser probe or the like which does not require guiding light. Also, this mode has a good effect on the elimination of the fixed pattern noise.

Next, the operation of the ¾ removing mode will be explained.

In the completely removing mode, each imaging time of the C frame and D frame of the imaging frame was 1/60 second; however, in the ¾ removing mode as shown in FIG. 2(e), the imaging time of the C frame is 5/240 second and the imaging time of the D frame is 3/240 second, so that the C frame is imaged for 2/240 second longer. Therefore, a C frame period which is affected by the laser beam is 2/240 second longer than a D frame period in 8/240 (1/30) second of the sum of the C frame period and D frame period. That is, it is adjusted that the mode is affected by the laser beam only for 2/240 (1/120) second in 8/240 (1/30) second. This is because, for example, when a non-contact type laser probe is used, a guiding light including visible light, such as He—Ne, should be radiated to identify a laser irradiated portion and then, the guiding light is completely removed if the completely removing mode is set. In this mode, only ¼ of the effect of the laser beam and guiding light is left. Also, the timing of the illumination and non-illumination of the illuminating light and indicated output is the same as in the aforesaid completely removing mode. Then, the same effect as the completely removing mode can be obtained.

As mentioned above, according to the first embodiment, while the illumination and non-illumination of the illuminating light are repeated by a constant cycle, the rising of the C frame of the imaging frame and the falling of the D frame of the imaging frame are synchronized to adjust the percentage of the C frame and D frame of the imaging frame, so that an observation image having no effect or a little effect of a laser beam and burning light can be displayed on the monitor picture plane. As a result, an operator can observe a real-time state of a treatment part in order to prevent the treatment part from bleeding or perforating by deep cauterization or prevent the other parts from cauterizing.

Also, according to the first embodiment, the directly reflected light from the cautery part has a small incident angle to a band cut filter. The effect of the directly reflected light is removed mainly by the band cut filter. Scattered light has a large incident angle to the band cut filter and penetrates the filter. It is not necessary to remove the scattered light (having a large incident angle) by the band cut filter, so that a cut wavelength range of the band cut filter can be narrowed. This is effective in minimizing the influence on color reproduction and brightness. Since flaws such as white spots and black spots, and fixed pattern noises can be removed, the percentage of non-defective CCD can be raised. In addition, an extensive dynamic range can be provided.

Further, the endoscope apparatus of the first embodiment is also effective when the inserted direction of an endoscope is different from the inserted direction of a laser probe at the surgical operation under observation by a laparoscope.

Further, when the endoscope apparatus of the first embodiment is used at a position easily affected by outside light, for example, in the buccal cavity, or used with not only light but also with X-rays and ultrasonic waves, the noise superimposed on an image signal is effectively removed so as to prevent a decline of contrast or deterioration of color.

In the first embodiment, although an Nd-YAG laser is used, other laser, for example, $CO_2$ or Ar-dye can be used. Also, the ratio of the C frame period to D frame period which is a percentage removing the effect of a laser beam can be adjusted alternatively by a rotary switch or a multistage switch.

Also, when a visible light laser, such as Ar-dye or KTP laser is used, a band cut filter corresponding to the wavelength of the laser can be provided in front of the CCD. Generally, regardless of a visible light laser or invisible light laser, a laser cautery part is positioned near the center of a picture plane. Therefore, a laser beam from the cautery part enters the band cut filter at right angles, that is, a state of small incident angle. When the wavelength range being cut by the band cut filter is tried to be narrowed, the light entering the filter perpendicularly is reflected; however, the light entering the filter at a certain angle is transmitted. At the time of laser cauterization, in addition to the direct reflection of the laser beam from the cautery part, the light reflected by the subject and each part in an endoscope optical system is variously scattered and enters the band cut filter at a certain angle, and then, transmitted. Here, the scattered light is very weak compared with the light directly reflected from the cautery part. Nevertheless, the scattered light easily becomes flared because it has strong outgoing laser beams.

When the CCD of a field accumulation and field read type is used instead of the CCD of a frame accumulation and frame read type, the A field and B field may be imaged during the C frame and D frame periods in the first embodiment, respectively, to make each frame by summing up the period. Further, when a transfer type CCD is used, the C frame period is divided into the first half and second half to conduct illumination in the first half and to conduct non-illumination in the second half. Then, an imaging signal can be read during the period. Also, because a time difference exists between the C frame and D frame, a blur is an anxiety; however, actually it is not a problem since the cautery treatment by using a laser is carried out only when the movement of the cautery part is little.

Further, the illuminating light having the light source which is itself repeatedly turned on and off can be used.

Also, observation means is not only provided at the tip of the insertable part but also can be used as observation means of an optical endoscope, such as an outside TV camera.

Next, the second embodiment will be explained.

Figure 4:
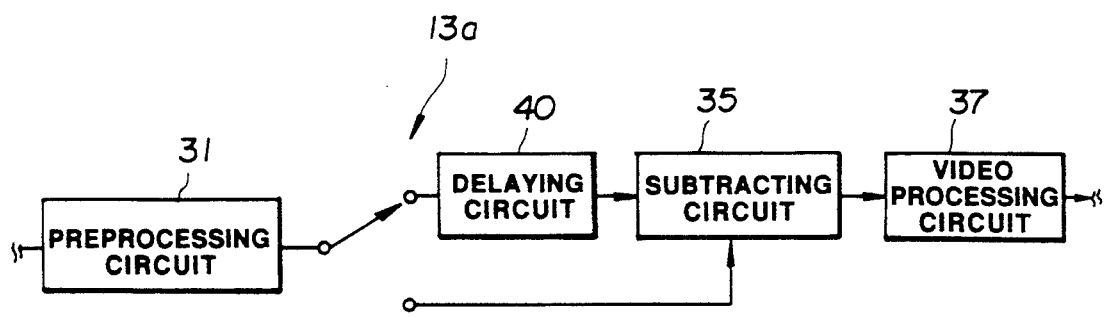
FIG. 4 is a block diagram showing the structure of a signal processing circuit related to the second embodiment.

The endoscope apparatus of the second embodiment has a different formation of the signal processing circuit but almost the same as in the first embodiment. That is, as shown in FIG. 4, after a signal processing circuit 13a is provided with a delay circuit 40 and a frame is delayed instead of the first memory 33 and the second memory 34 (see FIG. 1) used in the signal processing circuit 13 of the first embodiment, a difference signal is obtained by subtracting the process. The other formations are the same as in the first embodiment. Thus, similar operation and effects can be acquired.

Next, the third embodiment will be explained.

The endoscope apparatus of the third embodiment is formed using a frame sequential type endoscope.

Figure 6:
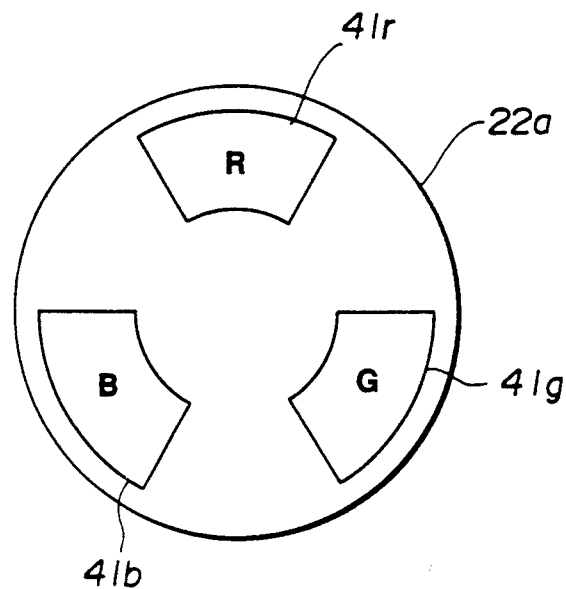

As shown in FIG. 5, a CCD 11a is a single plate CCD without having a color mosaic filter, and is a frame accumulation and read type CCD. Then, white illuminating light from a white illuminating lamp 23 is separated into R, G and B illuminating lights by a rotary filter 22a, for example, an R filter 41r, G filter 41g and B filter 41b shown in FIG. 6 to supply these lights sequentially in an endoscope apparatus 1a of the third embodiment.

Figure 7:
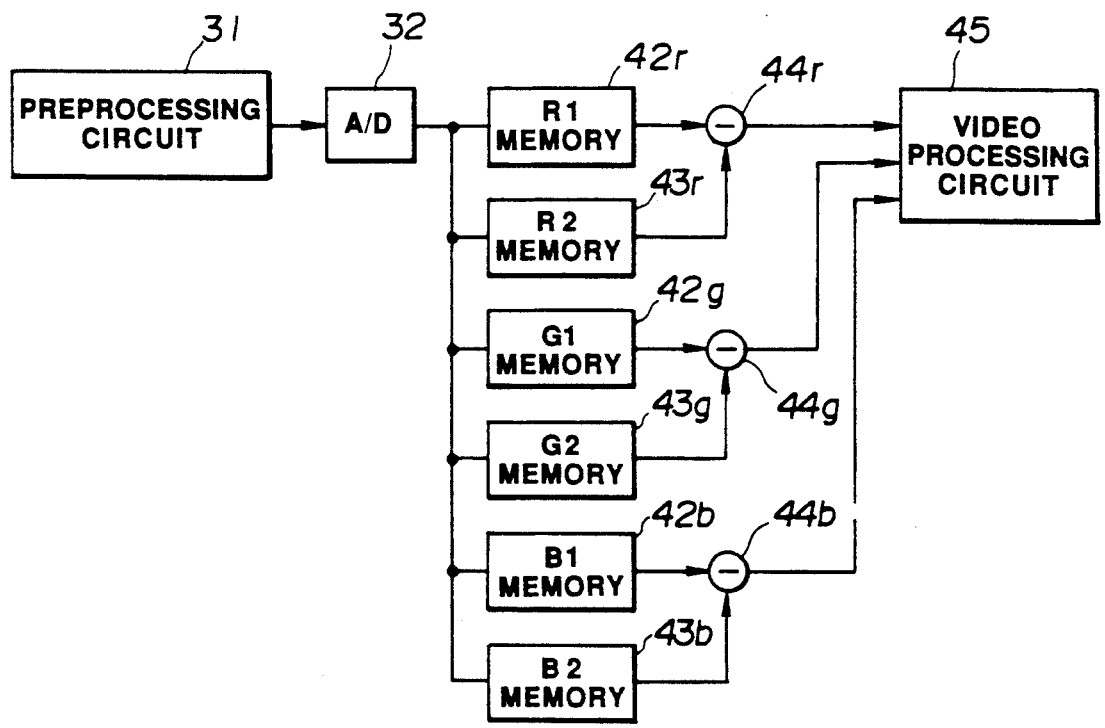

As shown in FIG. 7, a signal processing circuit 13b for processing an imaging signal for the CCD 11a imaged by the R, G and B illuminating lights comprises an R1 memory 42r, G1 memory 42g and B1 memory 42b for storing R, G and B color signals of an observation image, respectively, at illuminating a subject through a preprocessing circuit 31 and an A/D converter 32. An R2 memory 43r, G2 memory 43g and B2 memory 43b for storing R, G and B color signals of an observation image, respectively, at non-illuminating the subject, subtractors 44r, 44g and 44b for subtracting the signal when the subject is illuminated by each color and not illuminated and a video processing circuit 45 which supplies signals from the subtractors 44r, 44g and 44b, outputs these signals simultaneously and performs signal processing, such as $\gamma$ correction, to produce a standard video signal. Also, the R1 memory 42r, G1 memory 42g, B1 memory 42b, R2 memory 43r, G2 memory 43g and B2 memory 43b are synchronized with the rotary filter 22a and then, selected.

The other formations are the same as in the first embodiment.

The operation of the endoscope apparatus 1a of the third embodiment formed in this way will be explained.

Figure 8:
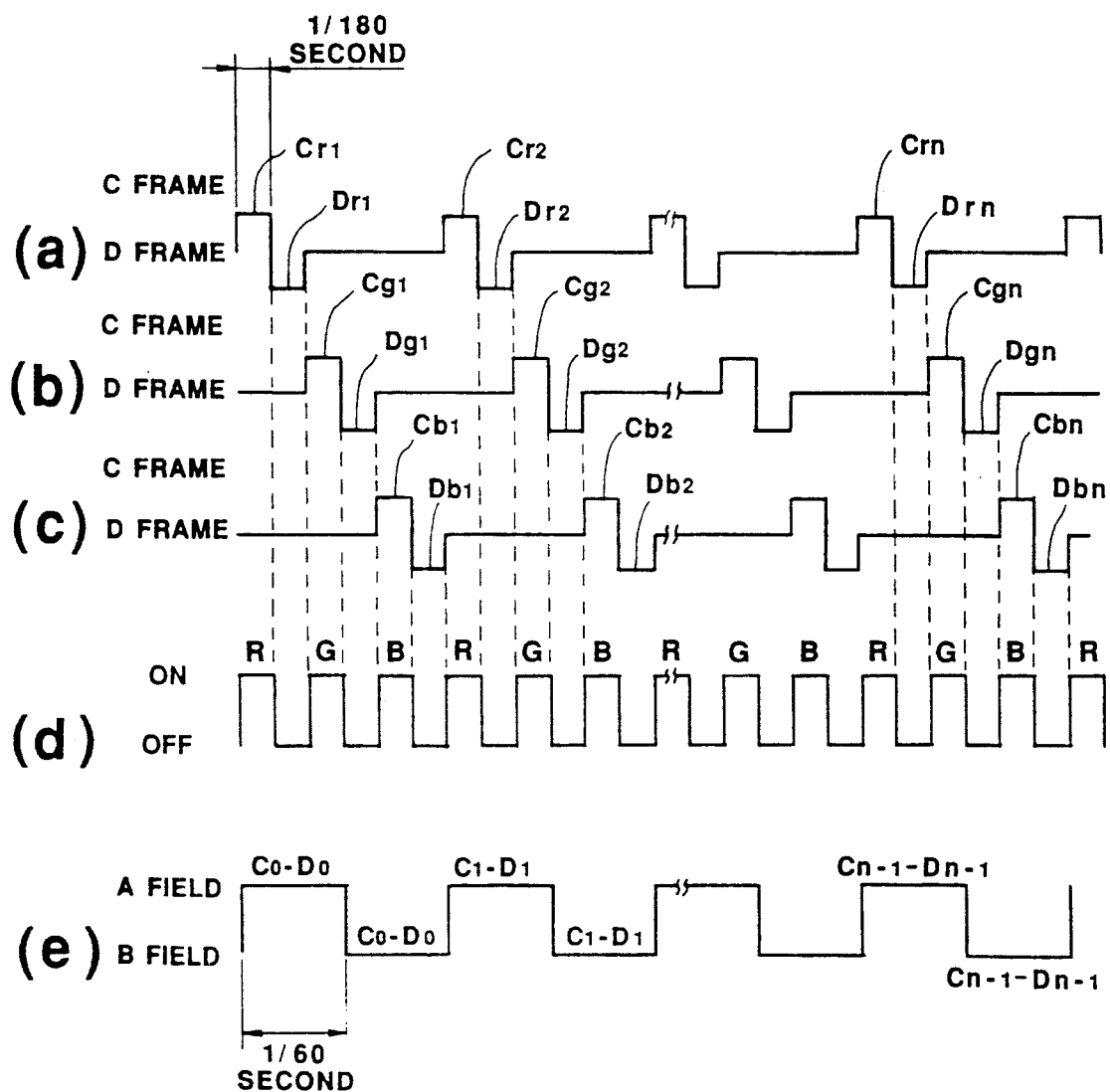

A completely removing mode of the endoscope apparatus 1a of the third embodiment repeats illumination and non-illumination at intervals of 1/180 second, so that the illuminating lights of frame sequential R, G and B are sent out as shown in FIG. 8(d). Then, for example, in the case of the R color signal, an R observation image is imaged on the C frame of the imaging frame during illumination, and on the D frame of the imaging frame during non-illumination, as shown in FIG. 8(a). That is, an observation image Cr1 when the R-illuminating light radiated is imaged on the C frame of the imaging frame and an observation image Dr1 when non-illuminating light radiated is imaged on the D frame.

Then, in the signal processing circuit 13b, Cr0−Dr0 in which an observation image Cr0 and Dr0 of 1/30 second before stored in the R1 memory 42r and the R2 memory 43r are subtracted by the subtractor 44r is fed to the video processing circuit 45. After the Cr0−Dr0 is fed, the Cr1 and Dr1 are stored in the R1 memory 42r and the R2 memory 43r. Similarly, the case of G and B color signals, the G and B observation images are imaged as shown in FIG. 8(b) and 8(c). Then, difference signals Cg0−Dg0 and Cb0−Db0 between the C frame and the D frame are fed to the video processing circuit 45.

In the video processing circuit 45, the Cr0−Dr0, Cg0−Dg0 and Cb0−Db0 being input are output simultaneously and processed, for example, $\gamma$ corrected, to produce a standard video signal and supplied into the monitor 16. As shown in FIG. 8(e), the image signal C0−D0 being output at the same time appears on the A and B field of the monitor 16. Accordingly, images are continuously displayed on the monitor 16 by the repeated process.

When the subject is periodically illuminated in this way, a laser for cauterizing is applied. Then, if R, G and B are summed up, respective laser radiating time for the C and D frames of the imaging frame becomes about a half of the total laser irradiating time as in the first embodiment. Therefore, the subject image illuminated only by illuminating light without having an effect of a laser beam or the like can be displayed on the monitor 16 as in the first embodiment. Also, the ¾ removing mode can be processed as in the first embodiment.

The other operation and effects are the same as in the first embodiment.

Although the signal processing circuit 13b of the third embodiment is formed using a plurality of memories, it can be also formed using a plurality of delay circuits as in the second embodiment. This invention is not restricted to a medical endoscope and also directed to an industrial endoscope.

In this invention, it is clear that working modes different in a wide range can be formed on the basis of this invention without departing from the spirit and scope of the invention. This invention is not restricted by its specific working modes except that it is limited by the appended claims.

What is claimed is:

1. An endoscope apparatus comprising:
   an insertable part adapted to be inserted into an object;
   illuminating means transmitting illuminating light through said insertable part, for periodically illuminating an object according to a cycle having an illuminating period and a non-illuminating period;
   imaging means for imaging the object during said illuminating period and said non-illuminating period;
   means for at least partially removing the effect of illumination other than said illuminating light including signal operating means for producing a difference signal between an imaging signal from said imaging means in a first period, including at least a part of said illuminating period in a cycle of said illuminating period and said non-illuminating period, and an imaging signal from said imaging means in a second period, including at least a part of said non-illuminating period in a cycle of said illuminating period and said non-illuminating period; and
   video signal producing means for producing a video signal from said difference signal of said signal operating means.

2. The endoscope apparatus according to claim 1, further comprising irradiating means for irradiating said subject by a laser beam, and said irradiating means sending out said laser beam during said illuminating period and said non-illuminating period.

3. The endoscope apparatus according to claim 2 wherein
   said imaging means includes a band cut filter for attenuating an amount of incident light of said laser beam.

4. The endoscope apparatus according to claim 2 wherein
   said laser beam radiated by said irradiating means is an NdYAD laser.

5. The endoscope apparatus according to claim 2 wherein
   said laser beam radiated by said irradiating means is a visible laser.

6. The endoscope apparatus according to claim 1 wherein
   said first period is equal to said illuminating period and
   said second period is equal to said non-illuminating period.

7. The endoscope apparatus according to claim 1,
   wherein said first period includes a period in which subsequent portions of said illuminating period and said non-illuminating period are added, and
   wherein said second period includes a period in which said first period is removed form a cycle of said illuminating period and said non-illuminating period.

8. The endoscope apparatus according to claim 1,
   wherein said illuminating means includes a white light source for sending out a white illuminating light, and
   wherein cutting off means for cutting off said white illuminating light periodically and for repeating said illuminating period and said non-illuminating period.

9. The endoscope apparatus according to claim 8,
   wherein said imaging means includes a separating means for separating said subject periodically illuminated for said illuminating period and said non-illuminating period by said cutting off means into a plurality of colors to image said subject.

10. The endoscope apparatus according to claim 1,
    wherein said illuminating means includes a sending means for sending out a plurality of illuminating lights having different wavelength ranges and illuminating the subject periodically for said illuminating period and said non-illuminating period in every light of said plurality of illuminating light having different wavelength ranges.

11. The endoscope apparatus according to claim 10,
    wherein said signal operating means includes an operating means for operating a difference signal between an imaging signal from said imaging means in said first period in every light of said plurality of illuminating light having different wavelength ranges and an imaging signal from said imaging means in said second period in every light of said plurality of illuminating light having different wavelength ranges, and
    wherein said video signal producing means includes an outputting means for simultaneously outputting said difference signal in every light of said plurality of illuminating light having different wavelength ranges from said signal operating means to produce a video signal.

12. The endoscope apparatus according to claim 9 or 11 wherein
    said signal operating means includes first memory means for storing a signal of said imaging means in said first period, said second memory means for storing a signal of said imaging means in said second period, and operating means for operating a difference between the signal stored in said first memory means and the signal stored in said second memory means.

13. The endoscope apparatus according to claim 12 wherein
    said first memory means and said second memory means convert a signal from said imaging means into a digital signal and store the digital signal.

14. The endoscope apparatus according to claim 9 or 11 wherein
    said signal operating means includes delay means for delaying a signal of said imaging means in said first period, a signal of said imaging means in said first period delayed by said delaying means and operating means for operating a difference between a signal of said imaging means in said first period delayed by said delaying means and a signal of said imaging means in said second period.

15. The endoscope apparatus according to claim 9 or 11 wherein said imaging means is a CCD of a frame accumulation and frame read type.

16. The endoscope apparatus according to claim 9 or 11, wherein said insertable part includes a hollow path in which a laser transmitting member transmitting a laser beam sent out near the object is inserted.

17. The endoscope apparatus according to claim 16 wherein said imaging means includes a band cut filter for attenuating an amount of incident light of the laser beam from said laser transmitting member inserted into said hollow path.

* * * * *